United States Patent
Yanagawa et al.

(10) Patent No.: US 9,388,096 B2
(45) Date of Patent: Jul. 12, 2016

(54) PRODUCING METHOD OF MONOCYCLIC AROMATIC HYDROCARBONS AND MONOCYCLIC AROMATIC HYDROCARBON PRODUCTION PLANT

(75) Inventors: Shinichiro Yanagawa, Tokyo (JP); Yasuyuki Iwasa, Tokyo (JP); Susumu Yasui, Yokohama (JP); Yoshishige Sugi, Yokohama (JP); Atsushi Fukui, Kawasaki (JP); Atsuro Nagumo, Kawasaki (JP); Osamu Hirohata, Yokohama (JP)

(73) Assignees: JX Nippon Oil & Energy Corporation, Tokyo (JP); CHIYODA CORPORATION, Yokohama-shi, Kanagawa (JP)

(*) Notice: Subject to any disclaimer, the term of this patent is extended or adjusted under 35 U.S.C. 154(b) by 232 days.

(21) Appl. No.: 14/119,609

(22) PCT Filed: May 24, 2012

(86) PCT No.: PCT/JP2012/063363
§ 371 (c)(1),
(2), (4) Date: Feb. 24, 2014

(87) PCT Pub. No.: WO2012/161272
PCT Pub. Date: Nov. 29, 2012

(65) Prior Publication Data
US 2014/0179968 A1 Jun. 26, 2014

(30) Foreign Application Priority Data
May 24, 2011 (JP) .................................. 2011-115640

(51) Int. Cl.
*C07C 4/16* (2006.01)
*C10G 35/02* (2006.01)
(Continued)

(52) U.S. Cl.
CPC . *C07C 4/06* (2013.01); *C10G 11/18* (2013.01); *C10G 35/14* (2013.01); *C10G 45/68* (2013.01);
(Continued)

(58) Field of Classification Search
CPC ........... C07C 4/16; C10G 35/02; C10G 35/14
USPC .......................... 585/407; 208/133, 134, 106
See application file for complete search history.

(56) References Cited

U.S. PATENT DOCUMENTS

| 3,654,140 A | 4/1972 | Griffel |
| 2009/0288985 A1* | 11/2009 | Long ..................... C10G 69/04 208/57 |
| 2012/0012504 A1 | 1/2012 | Minami et al. |

FOREIGN PATENT DOCUMENTS

| EP | 1734098 A1 | 12/2006 |
| JP | H11-193250 A | 7/1999 |

(Continued)

OTHER PUBLICATIONS

Office Action issued Mar. 3, 2015 in JP Application No. 2013-516440.
(Continued)

*Primary Examiner* — Thuan D Dang
(74) *Attorney, Agent, or Firm* — Panitch Schwarze Belisario & Nadel LLP (57) ABSTRACT

A producing method of monocyclic aromatic hydrocarbons in which reaction products including monocyclic aromatic hydrocarbons are produced by bringing an oil feedstock and an aromatic production catalyst into contact with each other, the oil feedstock having a 10 volume % distillation temperature of more than or equal to 140° C. and a 90 volume % distillation temperature of less than or equal to 380° C., the method including the steps of: introducing the oil feedstock into a fluidized-bed reaction apparatus housing the aromatic production catalyst; bringing the oil feedstock and the aromatic production catalyst into contact with each other in the fluidized-bed reaction apparatus; and introducing steam into the fluidized-bed reaction apparatus based on the introducing amount of the oil feedstock per hour.

2 Claims, 1 Drawing Sheet

(51) Int. Cl.
*C10G 35/14* (2006.01)
*C07C 4/06* (2006.01)
*C10G 45/68* (2006.01)
*C10G 45/70* (2006.01)
*C10G 11/18* (2006.01)

(52) U.S. Cl.
CPC ........ *C10G 45/70* (2013.01); *C10G 2300/1096* (2013.01); *C10G 2300/301* (2013.01); *C10G 2400/30* (2013.01)

(56) References Cited

FOREIGN PATENT DOCUMENTS

| JP | 2007-527937 A | 10/2007 |
|----|---------------|---------|
| JP | 2008527075 A  | 7/2008  |
| JP | 2008535106 A  | 8/2008  |
| WO | 2006073643 A1 | 7/2006  |
| WO | 2006107933 A1 | 10/2006 |
| WO | 2010109899 A1 | 9/2010  |
| WO | 2011118753 A1 | 9/2011  |

OTHER PUBLICATIONS

Int'l Search Report issued Aug. 28, 2012 in Int'l Application No. PCT/JP2012/063363.

Extended European Search Report issued Nov. 12, 2014 in EP Application No. 12790290.6.

Notice of Allowance issued Nov. 4, 2015 in JP Application No. 2013516440.

\* cited by examiner

PRODUCING METHOD OF MONOCYCLIC AROMATIC HYDROCARBONS AND MONOCYCLIC AROMATIC HYDROCARBON PRODUCTION PLANT

CROSS-REFERENCE TO RELATED APPLICATION

This application is a Section 371 of International Application No. PCT/JP2012/063363, filed May 24, 2012, which was published in the Japanese language on Nov. 29, 2012, under International Publication No. WO 2012/161272 A1, and the disclosure of which is incorporated herein by reference.

TECHNICAL FIELD

The present invention is related to a producing method of monocyclic aromatic hydrocarbons and a monocyclic aromatic hydrocarbon production plant.

Priority is claimed on Japanese Patent Application No. 2011-115640, filed May 24, 2011, the contents of which are incorporated herein by reference.

BACKGROUND ART

Methods of producing monocyclic aromatic hydrocarbons such as BTX (benzene, toluene and xylene) from an oil feedstock such as a cracked light oil (hereinafter light cycle oil and also abbreviated as "LCO") containing a large amount of polycyclic aromatics obtained from a fluid catalytic cracking (hereinafter also abbreviated as "FCC") unit, or a light naphtha or heavy naphtha or the like obtained from a crude oil distillation unit, using a catalytic aromatic production reaction that employs an aromatic production catalyst are already well known.

The production systems of aromatic hydrocarbons using aromatic production catalyst generally employ a fixed bed system, a moving bed system or a fluidized-bed system. In Patent Document 1, a producing method of monocyclic aromatic hydrocarbons employing fluidized-bed system is disclosed. In a fluidized-bed reaction apparatus employing fluidized-bed system, the aromatic production catalyst and the feedstock can maintain in a state of similar to a complete mixing, and the reaction temperature becomes easy to maintain uniformity. In addition, the aromatic production catalyst, which is deteriorated by coke in a case where the feedstock becomes heavier, is withdrawn appropriately from the fluidized-bed reaction reactor, an adhered coke is burned, and heating the aromatic production catalyst can therefore be performed smoothly.

PRIOR ART DOCUMENTS

Patent Documents

[Patent Document 1] Pamphlet of International publication No. 2010/109899

DISCLOSURE OF THE INVENTION

Problems to be Solved by the Invention

In the above fluidized-bed reaction apparatus, the aromatic production catalyst enters a fluidized-bed state because of the vapor of the oil feedstock. Thus, when there is a turndown of the oil feedstock, and the like, that is, when the introducing amount of the oil feedstock per hour decreases, the fluidity of the aromatic production catalyst decreases. If the reaction proceeds in this state, an excess cracking occurs due to long contacting time of the feedstock and the aromatic production catalyst, and it causes undesirable effects on the product quality. Here, "turndown" is the situation in which the introducing amount of the feedstock decreases over time.

As a countermeasure of the above, for example, lowering the temperature conditions or a method of reducing the catalyst bed height of the aromatic production catalyst, and the like, is considered, although control of the reaction (in particular, maintaining a fluidized state) is difficult and not practical.

The present invention has been made in view of the above problems, and the present invention provides a producing method of monocyclic aromatic hydrocarbons and a monocyclic aromatic hydrocarbon production plant in which a fluidized state of the aromatic production catalyst in the fluidized-bed reaction apparatus is maintained, even when a turndown of oil feedstock occurs.

Means for Solving the Problem

In order to solve the above problems, one aspect of the present invention provides a producing method of monocyclic aromatic hydrocarbons producing reaction products including monocyclic aromatic hydrocarbons by bringing an oil feedstock and an aromatic production catalyst into contact with each other, the oil feedstock having a 10 volume % distillation temperature of more than or equal to 140° C. and a 90 volume % distillation temperature of less than or equal to 380° C., the method including the steps of: introducing the oil feedstock into a fluidized-bed reaction apparatus housing the aromatic production catalyst; bringing the oil feedstock and the aromatic production catalyst into contact with each other in the fluidized-bed reaction apparatus; and introducing steam into the fluidized-bed reaction apparatus based on an introducing amount of the oil feedstock per hour.

In addition, the producing method of monocyclic aromatic hydrocarbons according to another aspect of the present invention further includes the step of adjusting the introducing amount of the steam per hour based on the difference amount of the introducing amount of the oil feedstock per hour, when the introducing amount of the oil feedstock per hour decreases more than a predetermined introducing amount.

In addition, the producing method of monocyclic aromatic hydrocarbons according to another aspect of the present invention includes the fluidized-bed reaction apparatus is provided with a fluidized-bed reactor housing the aromatic production catalyst, a heat tank heating the aromatic production catalyst withdrawn from the inside of the fluidized-bed reactor by a combustion, and a catalyst transfer pipe transferring the aromatic production catalyst heated at the heat tank, wherein in the step of introducing steam, the steam may be introduced into at least one of the fluidized-bed reactor and the catalyst transfer pipe.

In addition, another aspect of the present invention provides a monocyclic aromatic hydrocarbon production plant in which reaction products including monocyclic aromatic hydrocarbons are produced by bringing an oil feedstock and an aromatic production catalyst into contact with each other, the oil feedstock having a 10 volume % distillation temperature of more than or equal to 140° C. and a 90 volume % distillation temperature of less than or equal to 380° C., the production plant including: a fluidized-bed reaction apparatus housing the aromatic production catalyst, an oil feedstock introducing device in which the oil feedstock is introduced into the fluidized-bed reaction apparatus and the oil feedstock is contacted with the aromatic production catalyst, and a steam introducing device introducing steam into the fluidized-bed reaction apparatus based on an introducing amount of the oil feedstock per hour.

In addition, the monocyclic aromatic hydrocarbon production plant according to another aspect of the present invention further includes: a steam introducing amount adjusting device adjusting the introducing amount of steam per hour based on the difference amount of the introducing amount of the oil feedstock per hour, when the introducing amount of the oil feedstock per hour decreases more than a predetermined introducing amount.

In addition, the monocyclic aromatic hydrocarbon production plant according to another aspect of the present invention includes the fluidized-bed reaction apparatus provided with a fluidized-bed reactor housing the aromatic production catalyst, a heat tank heating the aromatic production catalyst withdrawn from the inside of the fluidized-bed reactor by a combustion, and a catalyst transfer pipe transferring the aromatic production catalyst heated at the heat tank, wherein the steam introducing device may introduce the steam into at least one of the fluidized-bed reactor and the catalyst transfer pipe.

Effects of the Invention

According to the producing method of monocyclic aromatic hydrocarbons and the monocyclic aromatic hydrocarbon production plant of the present invention, even if a turn-down of the oil feedstock, and the like, occurs, a fluidized state of the aromatic production catalyst in the fluidized-bed reaction apparatus is maintained and the contact time can be controlled properly.

EMBODIMENTS OF THE INVENTION

Figure 1:
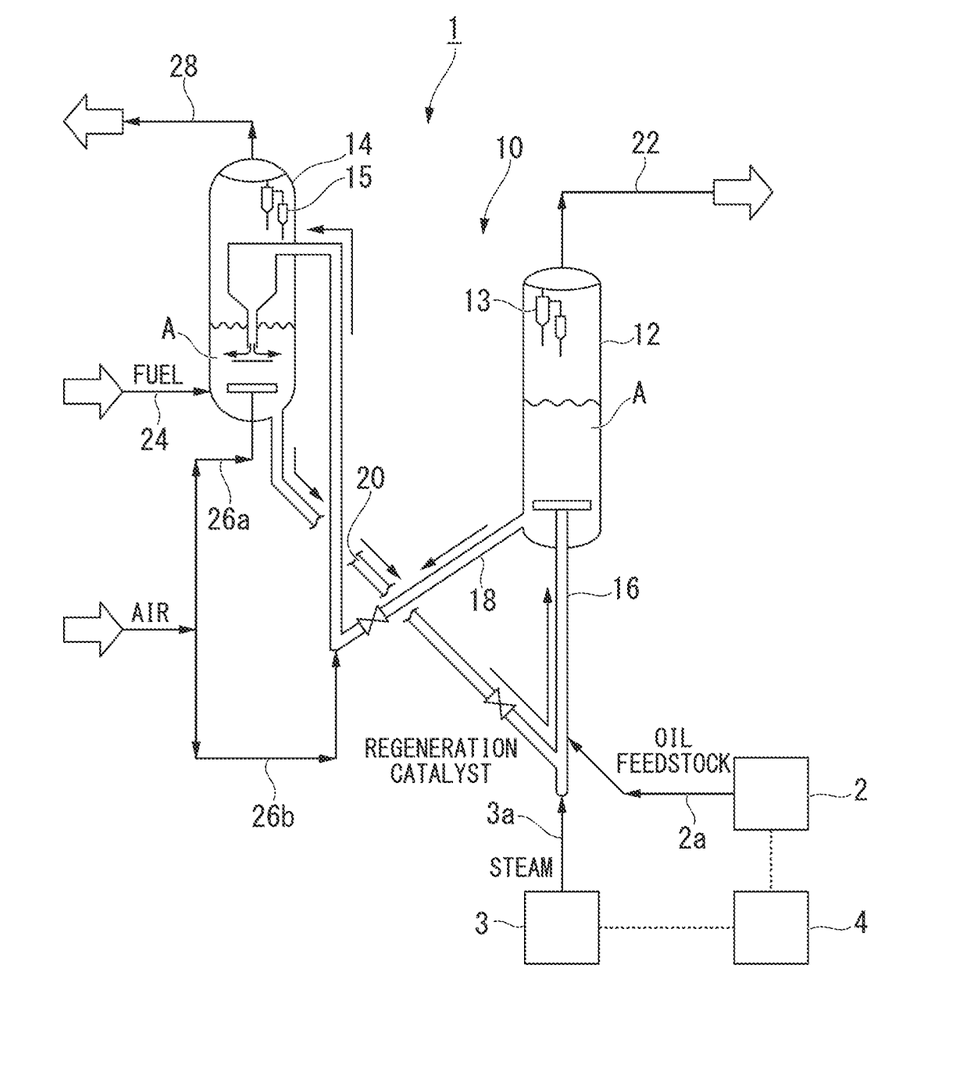
FIG. 1 is a schematic structural diagram illustrating one example of a monocyclic aromatic hydrocarbon production plant 1 according to the present invention.

<Monocyclic Aromatic Hydrocarbon Production Plant>
FIG. 1 is a schematic structural diagram illustrating one example of a monocyclic aromatic hydrocarbon production plant 1 according to the present invention.

The monocyclic aromatic hydrocarbon production plant 1 is provided with a fluidized-bed reaction apparatus 10, an oil feedstock introducing device 2, a steam introducing device 3, and a control device 4 (a steam introducing amount control device). The fluidized-bed reaction apparatus 10 is an apparatus in which an oil feedstock is brought into contact with an aromatic production catalyst A and thereby obtaining reaction products including monocyclic aromatic hydrocarbons, and is provided with a fluidized-bed reactor 12, a heating tank 14, and a catalyst riser 16 (a catalyst transfer pipe). In addition, the fluidized-bed reaction apparatus 10 is provided with a withdrawing pipe 18, a returning pipe 20, a reaction product pipe 22, a fuel pipe 24, an air pipe 26a, 26b, and an exhaust pipe 28. One end of the withdrawing pipe 18 is connected to the fluidized-bed reactor 12, and another end of the withdrawing pipe 18 is connected to the heating tank 14. One end of the returning pipe 20 is connected to the heating tank 14, and another end of the returning pipe 20 is connected to one end of the catalyst riser 16. One end of the reaction product pipe 22 is connected to the fluidized-bed reactor 12, and another end of the reaction product pipe 22 is connected to the distillation unit which is not shown. The fuel pipe 24 is connected to the heating tank 14. An air pipe is branched to an air pipe 26a and an air pipe 26b, and the air pipe 26a is connected to the heat tank 14 and the air pipe 26b is connected to the withdrawing pipe 18. The exhaust pipe 28 is connected to the heating tank 14.

The fluidized-bed reactor 12 is used for bringing the oil feedstock into contact with the fluidized bed-state aromatic production catalyst A to obtain a reaction product containing a large amount of BTX. The fluidized-bed reactor 12 includes a supply port, a withdrawing port, a cyclone 13, and a discharge port. The supply port of the fluidized-bed reactor 12 is a port through which a vapor of the oil feedstock and the aromatic production catalyst A that have been transported through the catalyst riser 16 are introduced into the inside of the fluidized bed reactor 12. The withdrawing port of the fluidized-bed reactor 12 is a port through which the aromatic production catalyst A is withdrawn and is connected to the withdrawing pipe 18. The cyclone 13 separates the reaction product vapor and the aromatic production catalyst A. The discharge port of the fluidized bed reactor 12 is a port through which the reaction product vapor separated by the cyclone 13 is discharged into the reaction product pipe 22.

The heating tank 14 is used for actively heating the aromatic production catalyst A, using not only the heat generated by combustion of the coke adhered to the aromatic production catalyst A, but also energy supplied from an external source. In other words, the heating tank 14 itself is a large heating unit. The heat tank 14 is provided with a first supply port, a withdrawing port, a second supply port, a third supply port, a cyclone 15, and an exhaust port. The first supply port of the heat tank 14 is a port through which the aromatic production catalyst A that has been transported through the withdrawing pipe 18 is introduced into the inside of the heat tank 14. The withdrawing port of the heating tank 14 is a port through which the aromatic production catalyst A is withdrawn from the heating tank 14 into the return pipe 20. The second supply port of the heating tank 14 is a port through which the tower bottom oil (heating fuel) and the like, supplied from, for example, the distillation unit which is not shown, via the fuel pipe 24 is introduced into the inside of the heating tank 14. The third supply port of the heat tank 14 is a port through which air (oxygen-containing gas) supplied from an air blower via the air pipe 26a is introduced into the inside of the heating tank 14. The cyclone 15 separates combustion gas generated by combustion and the aromatic production catalyst A. The exhaust port of the heating tank 14 is a port through which combustion gas separated by the cyclone 15 is exhausted from the heating tank 14 into the exhaust pipe 28.

The heating tank can be provided in a plurality of stages; for example in two stages. In other words, it is possible to take measures such as suppressing degradation of the aromatic production catalyst A by providing two heating tanks and increasing the heating temperature within the individual heating tanks in a stepwise manner.

The catalyst riser 16 is provided with a first supply port, a second supply port, and a third supply port. The catalyst riser 16 extends upward in a vertical direction and has a pipe shape, the first supply port thereof is a port through which the aromatic production catalyst A that has been transported through the return pipe 20 is introduced into the inside of the catalyst riser 16. The second supply port of the catalyst riser 16 is a port through which the oil feedstock that has been supplied through a feed pipe 2a is introduced into the inside of the catalyst riser 16. The third supply port of the catalyst riser 16 is a port through which steam that has been supplied through a steam pipe 3a is introduced into the inside of the catalyst riser 16.

The oil feedstock introducing device 2 introduces the oil feedstock that has transferred from the FCC unit and the like, which is not shown in the above fluidized-bed reaction apparatus 10. The oil feedstock introducing device 2 has the feed pipe 2a of which the end is connected to the catalyst riser 16. In addition, the oil feedstock introducing device 2 has a measurement device which is not shown and which measures an introducing amount of the oil feedstock per hour introduced through the feed pipe 2a. As the measurement device, if the introducing amount of the oil feedstock per hour can be measured, a device measuring the flow rate of the feedstock may be employed the flowmeter provided on the feed pipe 2a, for example. In addition, in a case where the oil feedstock introducing device 2 has a transferring device transferring the oil feedstock by a pump or a carrier gas and the like, a device, which calculates or estimates the introducing amount of the oil feedstock per hour from the driving command value for the transferring device, the actual driving state or performance of the transferring device and the like, can be employed.

The steam introducing device 3 introduces steam into the fluidized-bed reaction apparatus 10 based on the introducing amount of the oil feedstock per hour by the oil feedstock introducing device 2. The steam introducing device 3 has the steam pipe 3a of which the end is connected to the catalyst riser 16. The steam introducing device 3 may be configured to generate steam by itself by using a boiler and the like, and may be configured to be transferred steam generated at the other place in the plant. The steam-introducing device 3 has a valve, which is not shown, and the valve is provided on the steam pipe 3a, opens and shuts the flow thereof inside the steam pipe 3a. The valve can be operated so as to adjust the opening thereof at the steam pipe 3a in a stage manner or in a continuous manner.

The control device 4 adjusts the introducing amount of steam per hour from the steam introducing device 3 to an amount based on a difference amount which is between the introducing amount of the oil feedstock per hour and a predetermined introducing amount of the oil feedstock per hour, when the introducing amount of the oil feedstock per hour from the oil feedstock introducing device 2 decreases more than the predetermined introducing amount. The control device 4 has a computer system electrically connected to the measurement device of the oil feedstock introducing device 2 and the valve of the steam introducing device 3. The control device 4 of the present embodiment controls the valve stroke (opening) of the steam introducing device 3 based on the measurement result by the measurement device of the oil feedstock introducing device 2. In addition, the predetermined introducing amount has a meaning of the introducing amount of the oil feedstock per unit time which is required to maintain the fluidized state of the aromatic production catalyst A in the fluidized-bed reactor 12, in a certain operating condition.

<Producing Method of Monocyclic Aromatic Hydrocarbons>

Production of aromatic hydrocarbons using the production plant 1 illustrated in FIG. 1 is performed, for example, in the manner described below.

The oil feedstock is introduced continuously into the fluidized-bed reactor 12 from the feed pipe 2a. This oil feedstock may be in a gas-liquid two-phase state and the like, by heating the oil feedstock in advance using a pre-heater, which is not shown.

In addition, at the same time of introducing the oil feedstock, the aromatic production catalyst A heated by the heating tank 14 is introduced continuously into the catalyst riser 16 from the return pipe 20, and is transported into the fluidized-bed reactor 12 by the vapor of the oil feedstock, which rises up the inside of the catalyst riser 16 and acts as a transport medium.

The aromatic production catalyst A that is introduced continuously together with the vapor of the oil feedstock from the catalyst riser 16 to the fluidized-bed reactor 12 is converted to a fluidized-bed state by the vapor of the oil feedstock. The oil feedstock vapor and the aromatic production catalyst A are brought into contact with each other within this fluidized-bed state, yielding a reaction product vapor that contains a large amount of BTX. The reaction product vapor and the aromatic production catalyst A are separated by the cyclone 13, and the reaction product vapor is discharged continuously into the reaction product pipe 22. Coke adheres to the catalyst as a result of the contact with the oil feedstock vapor, and a portion of the partially inactivated aromatic production catalyst A is withdrawn continuously from the fluidized-bed reactor 12 into the withdrawing pipe 18.

By combusting the heating fuel, which is supplied from an external source through the fuel pipe 24, in the presence of the air (oxygen-containing gas) that is supplied from the air blower through the air pipe 26a, the aromatic production catalyst A that is introduced continuously into the heating tank 14 from the withdrawing pipe 18 is heated continuously to a temperature more than or equal to the reaction temperature inside the fluidized-bed reactor 12. Further, during this heating, the coke adhered to the aromatic production catalyst A also combusts, and thus, the aromatic production catalyst A undergoes regeneration during the heating process. The combustion gases generated by combustion are discharged continuously into the exhaust pipe 28. The aromatic production catalyst A heated by the heat tank 14 is withdrawn continuously from the heating tank 14 into the return pipe 20, and is then re-introduced into the catalyst riser 16 from the return pipe 20. In this manner, the aromatic production catalyst A is continuously circulated between the fluidized bed reactor 12 and the heating tank 14.

As the oil feedstock, at least one oils selected from the group consisting of LCO obtained from an FCC unit, the hydrotreated LCO, and naphtha and straight-run gas oil and the like obtained from a crude oil distillation unit is used. In those cases where these types of oil feedstock are used, the amount of coke that adheres to the aromatic production catalyst A upon bringing the oil feedstock and the aromatic production catalyst A into contact with each other is not necessarily sufficient to produce the amount of heat necessary to the cracking and reforming reactor 12 being supplied by combusting the coke. Accordingly, in order to enable efficient and stable production of a reaction product containing monocyclic aromatic hydrocarbons from the above types of oil feedstock, a fluidized-bed reaction apparatus 10 that includes a heating tank 14 is particularly effective.

(Steam Introducing Step)

In this way, in the producing plant 1 which is operated in a certain condition, when there is a turndown of the oil feedstock, and the like, that is, when the introducing amount of the feedstock per hour with respect to the fluidized-bed reaction apparatus 10 decreases, the fluidity of the aromatic production catalyst A, which is in a fluidized-bed state by the vapor of the feedstock, decreases in the fluidized-bed reactor 12. If the reaction proceeds in this state, the contacting time of the feedstock and the aromatic production catalyst A lengthens. For example, in a certain operating condition, when the introducing amount (a predetermined introducing amount) of the oil feedstock per unit time which is required to maintain the fluidized state of the aromatic production catalyst A in the fluidized-bed reactor 12 is assumed to be 100%, and if it decreases by 50% from 100%, the contacting time of oil feedstock and the aromatic production catalyst A in the fluidized-bed reactor 12 becomes, for example, approximately two times as long, and excess cracking and the like occurs. Thus, it causes undesirable effects on the product quality.

The steam is introduced by the steam introducing device 3 so as to correspond to changes of the contacting time and undesirable changes of the fluidized state in the fluidized-bed reactor 12 associated with the decreasing of the introducing amount of the oil feedstock per hour, and thus, the contacting time and the fluidized state are maintained by the introducing amount of the steam per hour. In addition, the steam is used actually as carrier gases and the like, in the plant, and it does not cause undesirable effects in the reaction.

(Steam Introducing Amount Adjusting Step)

The introducing amount of steam per hour by the steam introducing device 3 is adjusted by the control device 4. The control device 4 adjusts the introducing amount of steam per hour to an amount based on a difference amount which is between the introducing amount of the oil feedstock per hour and a predetermined introducing amount of the oil feedstock per hour when the introducing amount of the oil feedstock per hour decreases more than the predetermined introducing amount of the oil feedstock per hour. The control device 4 monitors the measurement result output from the measurement device of the oil feedstock introducing device 2, calculates the difference of the present introducing amount of the oil feedstock with respect to the predetermined amount of the oil feedstock, and controls the stroke (opening) of the valve of the steam introducing device 3 based on the difference. In this way, the control device 4 adjusts the introducing amount of steam introduced through the steam pipe 3a by adjusting the opening of the valve provided on the steam pipe 3a.

For example, when the introducing amount of the oil feedstock per hour decreased by 50% from 100% (the predetermined introducing amount of the oil feedstock per hour), the control device 4 adjusts the introducing amount of steam per hour from the steam introducing device 3 to an amount based on the difference amount which is between the introducing amount of the oil feedstock and the predetermined introducing amount of the oil feedstock and which is 50% in this case. In this way, even if the oil feedstock decreases by 50% from the predetermined introducing amount (100%), the same amount of steam, which is equal to 50% of the difference amount (decreased amount) of the oil feedstock, is introduced, and the difference amount of the oil feedstock is compensated for. Thus, in fluidized-bed reactor 12, the fluidized state of the aromatic production catalyst A can be maintained to a fluidized state suitable for the operation condition. As a result, even if the introducing amount of the oil feedstock per hour decreases, the contacting time (a fluidized state) between the oil feedstock and the aromatic production catalyst A in the fluidized-bed reactor 12 can be maintained constant, and thus, excess cracking does not occur, and a product quality of the reaction products can be maintained in a good state. This fluidized state suitable for the operation condition and maintaining a constant contacting time are adjusted by increasing the introducing amount of steam associated with the decreasing of the flow of the oil feedstock. In this case, it is preferable that the total of each molar equivalent be controlled so as to be constant. The relational expression (A) is described below.

$$(W\text{oil}/MW\text{oil}) + (W\text{steam}/MW\text{steam}) = \text{Const.} \quad (A)$$

wherein

Woil: flow rate of the oil feedstock [kg/h],

MWoil: average molecular weight of the oil feedstock [kg/kgmol],

Wsteam: flow rate of steam [kg/h], and

MWsteam: molecular weight of steam [kg/kgmol].

In addition, when the const. value is K in the above expression (A), it is preferable that the range of the value be 0.5K to 1.5K, and it is more preferable that the range of the value be 0.8K to 1.2K. That is, by setting and controlling the steam amount to be in a range in accordance with the change in the amount of oil feedstock, the fluidized state of the aromatic production catalyst A and the contacting time of the oil feedstock and the aromatic production catalyst A can be maintained smoothly.

The specific examples of the operation condition of the plant according to the present invention are as follows.

(Oil Feedstock)

The oil feedstock used in the present invention is an oil having a 10 volume % distillation temperature of more than or equal to 140° C. and a 90 volume % distillation temperature of less than or equal to 380° C. With an oil having a 10 volume % distillation temperature of less than 140° C., the reaction involves production of monocyclic aromatic hydrocarbons from light compounds, and thus, it depart from the spirit of producing monocyclic aromatics from the oil feedstock containing polycyclic aromatic hydrocarbons in the plant according to the present invention. Further, if an oil having a 90 volume % distillation temperature of more than 380° C. is used, then the yield of monocyclic aromatic hydrocarbons tends to decrease, and the amount of coke deposition on the monocyclic aromatic hydrocarbon production catalyst tends to increase, causing a more rapid deterioration in the catalytic activity.

The 10 volume % distillation temperature of the oil feedstock is preferably more than or equal to 150° C., and the 90 volume % distillation temperature of the oil feedstock is preferably less than or equal to 360° C.

In this description, the 10 volume % distillation temperature and the 90 volume % distillation temperature refer to values measured in accordance with the methods prescribed in JIS K 2254 "Petroleum products—determination of distillation characteristics".

Examples of oil feedstock having a 10 volume % distillation temperature of more than or equal to 140° C. and a 90 volume % distillation temperature of less than or equal to 380° C. include cracked light oils (LCO) produced in a fluid catalytic cracking apparatus, hydrotreated refined oil of LCO, coal liquefaction oil, hydrocracked oil from heavy oils, straight-run kerosene, straight-run gas oil, coker kerosene, coker gas oil, and hydrocracked oil from oil sands.

Polycyclic aromatic hydrocarbons included in these oil feedstocks exhibit low reactivity and are difficult to convert to monocyclic aromatic hydrocarbons in the cracking and reforming reaction step of the present invention. On the other hand, these polycyclic aromatic hydrocarbons are hydrogenated in the hydrogenation reaction step and converted to naphthenobenzenes, and if these naphthenobenzenes are then recycled and re-supplied to the cracking and reforming reaction step, they can be converted to monocyclic aromatic hydrocarbons. However, among polycyclic aromatic hydrocarbons, tricyclic or higher-cyclic aromatic hydrocarbons consume a large amount of hydrogen in the hydrogenation reaction step, and suffer from poor reactivity in the cracking and reforming reaction step even in the form of a hydrogenation reaction product, and therefore the oil feedstock preferably does not contain a large amount of such tricyclic or higher-cyclic aromatic hydrocarbons. Accordingly, the amount of tricyclic or higher-cyclic aromatic hydrocarbons within the oil feedstock is preferably less than or equal to 25 volume %, and more preferably less than or equal to 15 volume %.

Examples of particularly desirable oil feedstock which contain bicyclic aromatic hydrocarbons that can be converted to naphthenobenzenes in the hydrogenation reaction step, but in which the amount of tricyclic or higher-cyclic aromatic hydrocarbons is reduced, include oil feedstock having a 90 volume % distillation temperature of more than or equal to 330° C.

In this description, the polycyclic aromatic hydrocarbons describe the combined total of the amount of bicyclic aromatic hydrocarbons (the bicyclic aromatics) and the amount of tricyclic or higher-cyclic aromatic hydrocarbons the tricyclic or higher-cyclic aromatics), which is either measured in accordance with JPI-5S-49 "Petroleum Products—Determination of Hydrocarbon Types—High Performance Liquid Chromatography", or determined by analysis using FID gas chromatography or two-dimensional gas chromatography. In the following description, an amount of polycyclic aromatic hydrocarbons, bicyclic aromatic hydrocarbons or tricyclic or higher-cyclic aromatic hydrocarbons reported using the units "volume % (vol %)" represents an amount that has been measured in accordance with JPI-5S-49, whereas an amount that is reported using the units "% by mass" represents an amount that has been measured on the basis of FID gas chromatography or two-dimensional gas chromatography.

(Aromatic Production Catalyst)

The aromatic production catalyst A is a catalyst for producing the monocyclic aromatic hydrocarbon and contains a crystalline aluminosilicate.

[Crystalline Aluminosilicate]

The crystalline aluminosilicate is preferably a medium pore size zeolite and/or a large pore size zeolite, as these materials enable the yield of the monocyclic aromatic hydrocarbons to be further increased.

Medium pore size zeolites are zeolites having a 10-membered ring basic structure, and examples of these medium pore size zeolites include zeolites having AEL, EUO, FER, HEU, MEL, MFI, NES, TON and WEI type crystal structures. Among these, MFI-type zeolites are preferable as they enable a greater increase in the yield of monocyclic aromatic hydrocarbons.

Large pore size zeolites are zeolites having a 12-membered ring basic structure, and examples of these large pore size zeolites include zeolites having AFI, ATO, BEA, CON, FAU, GME, LTL, MOR, MTW and OFF type crystal structures. Among these, BEA, FAU and MOR type zeolites are preferred in terms of industrial usability, and BEA-type zeolites are desirable as they enable a greater increase in the yield of monocyclic aromatic hydrocarbons.

Besides the above medium pore size zeolites and large pore size zeolites, the crystalline aluminosilicate may also contain small pore size zeolites having a 10-membered ring or smaller basic structure, and extra-large pore size zeolites having a 14-membered ring or a larger basic structure.

Examples of the small pore size zeolites include zeolites having ANA, CHA, ERI, GIS, KFI, LTA, NAT, PAU and YUG type crystal structures.

Examples of the extra-large pore size zeolites include zeolites having CLO and VPI type crystal structures.

In those cases where the cracking and reforming reaction step is conducted as a fluidized-bed reaction, the amount of the crystalline aluminosilicate within the monocyclic aromatic hydrocarbon production catalyst, relative to a value of 100% by mass for the entire catalyst, is preferably within a range from 20 to 60% by mass, more preferably from 30 to 60% by mass, and still more preferably from 35 to 60% by mass. Provided the amount of the crystalline aluminosilicate is at least 20% by mass, the yield of monocyclic aromatic hydrocarbons can be increased satisfactorily. However, if the amount of the crystalline aluminosilicate exceeds 60% by mass, then the amount of binder that can be included in the catalyst decreases, and the resulting catalyst may be unsuitable for a fluidized-bed.

In addition, in those cases where the cracking and reforming reaction step is conducted as a fixed bed reaction, the amount of the crystalline aluminosilicate within the monocyclic aromatic hydrocarbon production catalyst, relative to a value of 100% by mass for the entire catalyst, is preferably within a range from 60 to 100% by mass, more preferably from 70 to 100% by mass, and still more preferably from 90 to 100% by mass. Provided the amount of the crystalline aluminosilicate is at least 60% by mass, the yield of monocyclic aromatic hydrocarbons can be increased satisfactorily.

[Phosphorus, Boron]

The monocyclic aromatic hydrocarbon production catalyst preferably includes phosphorus and/or boron. If the monocyclic aromatic hydrocarbon production catalyst includes phosphorus and/or boron, then a deterioration over time in the yield of monocyclic aromatic hydrocarbons can be prevented, and coke production on the catalyst surface can be inhibited. In addition, in a case where steam is introduced as the present embodiment, a deterioration due to hydrothermal reaction may occur in the fluidized-bed reactor 12, and thus, a catalyst containing phosphorus and/or boron is more preferable.

The methods for incorporating phosphorus within the monocyclic aromatic hydrocarbon production catalyst include methods in which phosphorus is supported on a crystalline aluminosilicate, crystalline aluminogallosilicate or crystalline aluminozincosilicate, methods in which a phosphorus compound is added during synthesis of the zeolite, thereby substituting a portion of the internal framework of the crystalline aluminosilicate with phosphorus, and methods in which a crystallization promoter containing phosphorus is used during synthesis of the zeolite, by ion-exchange methods and impregnation methods, for example. Although there are no particular limitations on the phosphate ion-containing aqueous solution used in the above methods, an aqueous solution prepared by dissolving phosphoric acid, diammonium hydrogen phosphate, ammonium dihydrogen phosphate or another water-soluble phosphate salt or the like in water at an arbitrary concentration can be used particularly favorably.

The methods for incorporating boron within the monocyclic aromatic hydrocarbon production catalyst include methods in which boron is supported on a crystalline aluminosilicate, crystalline aluminogallosilicate or crystalline aluminozincosilicate, methods in which a boron compound is added during synthesis of the zeolite, thereby substituting a portion of the internal framework of the crystalline aluminosilicate with boron, and methods in which a crystallization promoter containing boron is used during synthesis of the zeolite, by ion-exchange methods and impregnation methods, for example.

The amount of phosphorus and boron included in the monocyclic aromatic hydrocarbon production catalyst, relative to the total mass of the catalyst, is preferably within a range from 0.1 to 10% by mass, wherein the lower limit is more preferably not less than 0.5% by mass, and the upper limit is more preferably not more than 9% by mass, and still more preferably not more than 8% by mass. Provided the amount of phosphorus relative to the total mass of the catalyst is at least 0.1% by mass, any deterioration over time in the yield of the monocyclic aromatic hydrocarbons can be prevented, and provided the amount of phosphorus is not more than 10% by mass, the yield of the monocyclic aromatic hydrocarbons can be increased.

[Gallium, Zinc]

If necessary, gallium and/or zinc may be included in the monocyclic aromatic hydrocarbon production catalyst. Including gallium and/or zinc can improve the rate of production of monocyclic aromatic hydrocarbons.

Examples of the form of the gallium contained within the monocyclic aromatic hydrocarbon production catalyst include catalysts in which the gallium is incorporated within the lattice framework of the crystalline aluminosilicate (crystalline aluminogallosilicates), catalysts in which gallium is supported on the crystalline aluminosilicate (gallium-supporting crystalline aluminosilicates), and catalysts including both of these forms.

Examples of the form of the zinc contained within the monocyclic aromatic hydrocarbon production catalyst include catalysts in which the zinc is incorporated within the lattice framework of the crystalline aluminosilicate (crystalline aluminozincosilicates), catalysts in which zinc is supported on the crystalline aluminosilicate (zinc-supporting crystalline aluminosilicates), and catalysts including both of these forms.

A crystalline aluminogallosilicate or a crystalline aluminozincosilicate has a structure in which $SiO_4$, $AlO_4$, and $GaO_4$ structures exist within the framework. In addition, a crystalline aluminogallosilicate or crystalline aluminozincosilicate can be obtained, for example, by gel crystallization via hydrothermal synthesis, by a method in which gallium or zinc respectively is inserted into the lattice framework of a crystalline aluminosilicate, or a method in which aluminum is inserted into the lattice framework of a crystalline gallosilicate or crystalline zincosilicate respectively.

A gallium-supporting crystalline aluminosilicate can be obtained by supporting gallium on a crystalline aluminosilicate using a conventional method such as an ion-exchange method or impregnation method. There are no particular limitations on the gallium source used in these methods, and examples include gallium salts such as gallium nitrate and gallium chloride, and gallium oxide.

A zinc-supporting crystalline aluminosilicate can be obtained by supporting zinc on a crystalline aluminosilicate using a conventional method such as an ion-exchange method or impregnation method. There are no particular limitations on the zinc source used in these methods, and examples include zinc salts such as zinc nitrate and zinc chloride, and zinc oxide.

In those cases where the monocyclic aromatic hydrocarbon production catalyst contains gallium and/or zinc, the amount of gallium and zinc within the monocyclic aromatic hydrocarbon production catalyst, relative to a value of 100% for the total mass of the catalyst, is preferably within a range from 0.01 to 5.0% by mass, and more preferably from 0.05 to 2.0% by mass. Provided the amount of gallium and/or zinc is more than or equal to 0.01% by mass, the rate of production of monocyclic aromatic hydrocarbons can be increased, and provided the amount is less than or equal to 5.0% by mass, the yield of monocyclic aromatic hydrocarbons can be improved.

[Form]

The monocyclic aromatic hydrocarbon production catalyst is used in the form of a powder, granules or pellets or the like, depending on the reaction format. For example, a catalyst in form of powder is used in the case of a fluidized bed represented as the present embodiment, whereas a catalyst in form of granules or pellets is used in the case of a fixed bed represented as other embodiments. The average particle size of the catalyst used in a fluidized bed is preferably within a range from 30 to 180 μm, and more preferably from 50 to 100 μm. Further, the powder density of the catalyst used in a fluidized bed is preferably within a range from 0.4 to 1.8 g/cc, and more preferably from 0.5 to 1.0 g/cc.

The average particle size describes the particle size at which the particle size distribution obtained by classification using sieves reaches 50% by mass, whereas the powder density refers to the value measured using the method prescribed in JIS R 9301-2-3.

In order to obtain a catalyst in granular or pellet form, if necessary, an inert oxide may be added to the catalyst as a binder, with the resulting mixture then molded using any of various molding apparatus.

In those cases where the monocyclic aromatic hydrocarbon production catalyst contains an inorganic oxide such as a binder, a compound that contains phosphorus may be used as the binder.

The heating fuel acts as an additional fuel besides the coke adhered to the aromatic production catalyst A, and examples of this heating fuel include fuels supplied from externally (so-called torch oil), such as the tower bottom oil from the distillation unit. In terms of avoiding the problem of degradation of the aromatic production catalyst A caused by steam, the heating fuel is preferably a tower bottom oil having a comparatively large ratio of carbon atoms to hydrogen atoms (C/H).

Examples of the oxygen-containing gas include air and pure oxygen, although air is preferable from an economic viewpoint.

Because the heat required by the aromatic production reaction inside the fluidized bed reactor 12 is supplied by the aromatic production catalyst A heated by the heat tank 14, the heating of the oil feedstock by the preheating unit may be performed to any temperature less than the reaction temperature inside the fluidized bed reactor 12, and is preferably within a range from 150 to 350° C.

(Reaction Temperature)

Although there are no particular limitations on the reaction temperature during contact of the oil feedstock with the monocyclic aromatic hydrocarbon production catalyst and subsequent reaction, a reaction temperature of 400 to 650° C. is preferable. Provided the lower limit for the reaction temperature is at least 400° C., the oil feedstock can be reacted with relative ease. The lower limit is more preferably 450° C. or higher. On the other hand, provided the upper limit temperature is not more than 650° C., the yield of monocyclic aromatic hydrocarbons can be increased. The upper limit is more preferably 600° C. or lower.

(Reaction Pressure)

The reaction pressure during contact of the oil feedstock and a recycle oil described hereafter with the monocyclic aromatic hydrocarbon production catalyst and subsequent reaction is preferably less than or equal to 1.5 MPaG, and more preferably less than or equal to 1.0 MPaG. Provided the reaction pressure is not more than 1.5 MPaG, the generation of by-product light gases can be prevented, and the pressure resistance required for the reaction apparatus can be lowered.

(Contact Time)

There are no particular limitations on the contact time between the oil feedstock and the monocyclic aromatic hydrocarbon production catalyst, provided the desired reaction proceeds satisfactorily, but in terms of the gas transit time across the monocyclic aromatic hydrocarbon production catalyst, a time of 1 to 300 seconds is preferred. The lower limit for this time is more preferably more than or equal to 5 seconds, and the upper limit is more preferably less than or equal to 150 seconds. Provided the contact time is more than or equal to 1 second, a reliable reaction can be achieved, whereas provided the contact time is less than or equal to 300 seconds, deposition of carbon matter on the catalyst due to an excess coking or the like can be suppressed, and the amount of light gas generated by cracking can also be suppressed.

The amount of the aromatic production catalyst A withdrawn from the fluidized bed reactor 12 (namely, the circulation amount) is preferably within a range from 5 to 30 tons per 1 ton of the oil feedstock supplied to the fluidized bed reactor 12. This amount is also determined in accordance with the overall heat balance.

The pressure inside the heating tank 14 is preferably higher than the pressure inside the fluidized-bed reactor 12 in order to facilitate transport of the heated aromatic production catalyst A heated by the heating tank 14 to the fluidized bed reactor 12.

In the case of a two-stage heating process, if the first heating tank is located in a lower position than the second heating tank, then the pressure inside the first heating tank must be set to a higher pressure than that inside the second heating tank to enable transport of the aromatic production catalyst A heated by the heating tank 14 into the second heating tank. The pressure inside the first heating tank 14 is preferably approximately 0.1 MPa higher than the pressure inside the second heating tank, and is preferably more than or equal to 0.2 MPa, and more preferably more than or equal to 0.9 MPa.

The lower limit for the pressure inside the second heating tank is preferably 0.1 MPaG, more preferably 0.2 MPaG, and still more preferably 0.3 MPaG. The upper limit is preferably 0.8 MPaG, more preferably 0.7 MPaG, and still more preferably 0.6 MPaG.

Because the heat required by the aromatic production reaction inside the fluidized bed reactor 12 is supplied by the aromatic production catalyst A heated by the heating tank 14, the temperature inside the heating tank 14 must be at least as high as the reaction temperature inside the fluidized bed reactor 12, and is preferably within a range from 500 to 800° C., and more preferably from 600 to 700° C.

In the case of a two-stage heating process, because the heat required by the aromatic production reaction inside the fluidized bed reactor 12 must be supplied by the aromatic production catalyst A heated by the heating tanks, the temperature of the first heating tank is preferably more than or equal to the reaction temperature inside the fluidized bed reactor 12. Further, in order to suppress hydrothermal degradation of the aromatic production catalyst A by the high-temperature steam generated upon combustion of the heating fuel, the temperature inside the first heating tank is preferably lower than the temperature inside the second heating tank. Specifically, the temperature inside the first heating tank is preferably less than or equal to 650° C., and more preferably less than or equal to 630° C.

Because the heat required by the aromatic production reaction inside the fluidized bed reactor 12 is supplied by the aromatic production catalyst A heated by the heating tanks, the lower limit for the temperature inside the second heating tank is preferably the reaction temperature inside the fluidized bed reactor 12, and is more preferably 500° C., and still more preferably 600° C. In contrast, the upper limit for the temperature is preferably 800° C., and more preferably 700° C.

The amount of the heating fuel supplied to the heating tank 14 (in the case of a tower bottom oil) is preferably within a range from 0.005 to 0.08 tons, per 1 ton of the oil feedstock supplied to the fluidized bed reactor 12, with this amount being determined in accordance with the amount of coke deposited and the overall heat balance.

In the case of a two-stage heating process, as a general principle, the total amount of the heating fuel is preferably supplied to the first heating tank.

In the producing method of monocyclic aromatic hydrocarbons in the present invention described as above, the method includes the steps of introducing the oil feedstock having a 10 volume % distillation temperature of more than or equal to 140° C. and a 90 volume % distillation temperature of less than or equal to 380° C. into the fluidized-bed reaction apparatus 10, bringing the oil feedstock and the aromatic production catalyst A into contact with each other, and producing reaction products including monocyclic aromatic hydrocarbons, and the method includes the step of introducing steam into the fluidized-bed reaction apparatus 10 based on the introducing amount of the oil feedstock per hour. Accordingly, even in a case where the introducing amount of the oil feedstock changes, it can inhibit undesirable effects of the reaction caused by the changes, by introducing steam instead of the oil feedstock.

Therefore, according to the present invention, without lowering the conditions of the temperature and the catalyst bed height and the like, the reaction inside the fluidized-bed reactor 12 of the fluidized-bed reaction apparatus 10 can be controlled stably by adjusting the introducing amount of the steam. In addition, even in a case where a turndown of the oil feedstock and the like occurs, the fluidized state of the aromatic production catalyst A can be maintained constant.

Hereafter, the effects of the mixing (co-existing) of the oil feedstock and steam are explained with referring to the Table 1.

TABLE 1

| Oil feedstock properties | | | | Analyzing method |
|---|---|---|---|---|
| Density at 15° C. | | g/cm³ | 0.9258 | JIS K 2249 |
| Dynamic viscosity at 30° C. | | mm²/s | 2.817 | JIS K 2283 |
| Distillation properties | Initial distillation point | ° C. | 173 | JIS K 2254 |
| | 10 vol % distillation temperature | ° C. | 215 | |
| | 50 vol % distillation temperature | ° C. | 266 | |
| | 90 vol % distillation temperature | ° C. | 318 | |
| | End point | ° C. | 346 | |
| Composition analysis | Saturated compounds | vol % | 22.9 | JPI-5S-49 |
| | Olefin compounds | vol % | 2.1 | |
| | Whole aromatics | vol % | 75 | |
| | Monocyclic aromatics | vol % | 27.6 | |
| | Bicyclic aromatics | vol % | 39.5 | |
| | Tricyclic or higher-cyclic aromatics | vol % | 7.9 | |

EXAMPLE

Under the conditions of: a gas flow ratio of LCO (10 volume % distillation temperature: 215° C., and 90 volume % distillation temperature: 318° C.), which is an oil feedstock and is shown in Table 1, and steam is 2:1; a reaction temperature is 538° C.; a reaction pressure is 0.3 MPaG; and a contacting time between the LCO and the zeolite component containing in the catalyst is 7 seconds, the oil feedstock reacts by contacting with the catalyst A (containing a binder in an MFI-type zeolite on which 0.2% by mass of gallium and 0.7% by mass of phosphorus is supported) in the fluidized-bed reactor, and a cracking and reforming reaction was performed.

As a result, the fluidized state was approximately the same fluidized state with comparing to a comparative example. The monocyclic aromatic hydrocarbons having 6 to 8 carbon atoms were captured from the product by steps of a gas-liquid separation and a distillation. The production amount of captured BTX was measured by using a two dimensions gas chromatography (ZOEX KT2006 GCxGC System), and it was 35% by mass.

COMPARATIVE EXAMPLE

Under the conditions of: supplying only LCO (10 volume % distillation temperature: 215° C., and 90 volume % distillation temperature: 318° C.), which is an oil feedstock and is shown in Table 1; a reaction temperature is 538° C.; a reaction pressure is 0.3 MPaG; and a contacting time between the LCO and the zeolite component containing in the catalyst is 7 seconds, the oil feedstock reacts by contacting with the catalyst A (containing a binder in an MFI-type zeolite on which 0.2% by mass of gallium and 0.7% by mass of phosphorus is supported) with the same amount to the example in the fluidized-bed reactor, and a cracking and reforming reaction was performed. In this case, the gas flow rate of LCO was approximately 1.5 times with respect to the flow rate of the example (that is, this LCO flow rate was the sum of the gas flow rate ratio of the steam and the LCO in the example). In addition, the monocyclic aromatic hydrocarbons having 6 to 8 carbon atoms were captured from the product by the steps of the gas-liquid separation and the distillation. The production amount of captured BTX was measured by using a two dimensions gas chromatography (ZOEX KT2006 GCxGC System), and it was 35% by mass.

According to the above result, in a case of mixing the steam, the reaction equivalent to a case of not mixing with the steam is in progress was confirmed. On the other hand, if the steam is not introduced and the flow rate that the oil feedstock is introduced at is equal to ⅔ (of the ⅔ flow rate of oil feedstock), it was confirmed that ensuring the equivalent flow state becomes difficult and maintaining a proper fluid state is not possible.

While exemplary embodiments of the invention have been described above with reference to the drawings, the above embodiments are not to be considered as limitative of the present invention. Shapes, combinations and the like of the constituent members illustrated in the above embodiments are merely examples, and various modifications based on design requirements and the like can be made without departing from the scope of the present invention.

For example, the steam introducing device 3 can introduce the steam into the fluidized-bed reactor 12 instead of the catalyst riser 16, introduce the steam into both the fluidized-bed reactor 12 and the catalyst riser 16, and can introduce the steam from a variety of heights in multiple stages.

In addition, for example, the catalyst riser 16 can be further provided for a turndown of the oil feedstock, the end of this catalyst riser 16 can be arranged inside the aromatic production catalyst A in the fluidized-bed reactor 12 and arranged at a higher position of the normal catalyst riser 16.

For example, normally, the oil feedstock is introduced from the normal catalyst riser 16 arranged at the lowest position, and when a turndown is performed, the turndown amount of the oil feedstock is introduced from the catalyst riser 16 for a turndown positioned at a higher position. Thus, a desirable contacting time and the fluidized state are maintained. Meanwhile, from the normal catalyst riser 16 arranged at the low position, it is preferable to introduce the steam instead of the oil feedstock or with a reduced amount of oil feedstock.

Furthermore, in order to introduce the oil feedstock, an introduction part is provided to the fluidized bed reactor 12 in various positions (upper position and lower position) so as to correspond to the turndown, and when a turndown from the introducing position (lower position) at a normal operation occurs, the oil feedstock can be introduced from upper position in order to control the contacting time.

DESCRIPTION OF REFERENCE SIGNS

1: monocyclic aromatic hydrocarbon production plant
2: oil feedstock introducing device
3: steam introducing device
4: steam introducing amount control device
10: fluidized-bed reaction apparatus
12: fluidized-bed reactor
14: heating tank
16: catalyst riser (catalyst transfer pipe)
A: aromatic production catalyst

The invention claimed is:

1. A producing method of monocyclic aromatic hydrocarbons in which reaction products including monocyclic aromatic hydrocarbons are produced by bringing an oil feedstock and an aromatic production catalyst into contact with each other, the oil feedstock having a 10 volume % distillation temperature of more than or equal to 140° C. and a 90 volume % distillation temperature of less than or equal to 380° C., the method comprising the steps of:
    introducing the oil feedstock into a fluidized-bed reaction apparatus housing the aromatic production catalyst;
    bringing the oil feedstock and the aromatic production catalyst into contact with each other in the fluidized-bed reaction apparatus;
    introducing steam into the fluidized-bed reaction apparatus based on an introducing amount of the oil feedstock per hour;
    when the introducing amount of the oil feedstock per hour decreases more than a predetermined introducing amount, adjusting the introducing amount of the steam per hour based on the difference amount of the introducing amount of the oil feedstock per hour; and
    producing the monocyclic aromatic hydrocarbons,
        wherein the step of adjusting the introducing amount of the steam is controlled by a relational expression defined as follows:

$$(Woil/MWoil)+(Wsteam/MWsteam)=constant$$

wherein:
        Woil: flow rate of the oil feed stock [kg/h],
        MWoil: average molecular weight of the oil feedstock [kg/kgmol],
        Wsteam: flow rate of steam [kg/h], and
        MWsteam: molecular weight of steam [kg/kgmol].

2. The producing method of monocyclic aromatic hydrocarbons according to claim 1, wherein the fluidized-bed reaction apparatus is provided with a fluidized-bed reactor housing the aromatic production catalyst, a heat tank heating the aromatic production catalyst withdrawn from the inside of the fluidized-bed reactor by a combustion, and a catalyst transfer pipe transferring the aromatic production catalyst heated at the heat tank to the fluidized-bed reactor, wherein in the step of introducing steam, the steam is introduced into at least one of the fluidized-bed reactor and the catalyst transfer pipe.

\* \* \* \* \*